United States Patent [19]

Floyd, Jr.

[11] Patent Number: 4,737,590

[45] Date of Patent: Apr. 12, 1988

[54] NOVEL 2-SUBSTITUTED-3,4-EPOXYCYCLOPENTAN-1-ONES, 2-SUBSTITUTED-3,4-EPOXYCYCLOPENTAN-1-OLS, AND VARIOUS 2-SUBSTITUTED-CYCLOPENTENONES

[75] Inventor: Middleton B. Floyd, Jr., Suffern, N.Y.

[73] Assignee: American Cyanamid Company, Stamford, Conn.

[21] Appl. No.: 268,178

[22] Filed: May 29, 1981

Related U.S. Application Data

[60] Division of Ser. No. 115,833, Jan. 28, 1980, Pat. No. 4,293,704, which is a continuation of Ser. No. 616,790, Sep. 25, 1975, Pat. No. 4,237,716, which is a continuation-in-part of Ser. No. 355,101, Apr. 27, 1973, abandoned.

[51] Int. Cl.[4] .............. C07F 7/08; C07F 7/18
[52] U.S. Cl. ........................ 556/438
[58] Field of Search .............. 556/436, 438, 437

[56] References Cited

U.S. PATENT DOCUMENTS

| | | | |
|---|---|---|---|
| 3,538,120 | 11/1970 | Finch | 556/441 X |
| 3,651,116 | 3/1972 | Lincoln et al. | 556/441 |
| 3,728,382 | 4/1973 | Bundy | 556/441 X |
| 3,772,350 | 11/1973 | Pike et al. | 556/441 |
| 3,822,303 | 7/1974 | Yankee | 556/441 |
| 3,849,487 | 11/1974 | Bundy | 556/441 X |
| 3,884,969 | 5/1975 | Schaub et al. | 556/441 X |
| 3,887,587 | 6/1975 | Schaaf et al. | 556/441 X |

Primary Examiner—Paul F. Shaver
Attorney, Agent, or Firm—Robert P. Raymond

[57] ABSTRACT

This disclosure describes novel 4-oxy-2-substituted-cyclopent-2-en-1-ones useful as intermediates for the preparation of homo and nor prostaglandins of the $E_2$, $E_3$ and F series.

6 Claims, No Drawings

NOVEL 2-SUBSTITUTED-3,4-EPOXYCYCLOPENTAN-1-ONES, 2-SUBSTITUTED-3,4-EPOXYCYCLOPENTAN-1-OLS, AND VARIOUS 2-SUBSTITUTED-CYCLOPENTENONES

CROSS REFERENCE TO RELATED APPLICATION

This is a division of application Ser. No. 115,833 filed Jan. 28, 1980, now U.S. Pat. No. 4,293,704 which is a continuation of Ser. No. 616,790 filed Sept. 25, 1975 now U.S. Pat. No. 4,237,716, which is a continuation-in-part of our copending application Ser. No. 355,101, filed Apr. 27, 1973 and now abandoned.

BRIEF SUMMARY OF THE INVENTION

This invention relates to novel 4-oxy-2-substituted-cyclopent-2-en-1-ones of the following general formula:

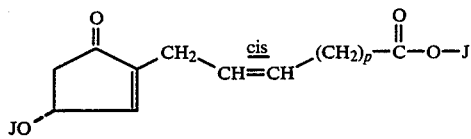

and the optical antipodes, racemic mixtures, and diastereomeric mixtures thereof wherein p is an integer from 2 to 6, inclusive, and J is hydrogen or an appropriate and compatible blocking group such as tetrahydropyranyl or tri(low alkyl)silyl. Suitable lower alkyl groups contemplated by the present invention are those having up to four carbon atoms such as methyl, ethyl, isopropyl, tert-butyl, etc.

DETAILED DESCRIPTION OF THE INVENTION

The novel 4-oxycyclopentenones of this invention may be readily prepared in accordance with the procedure set forth in Flowsheet A below and in which is also shown the transformation of a member of this class of compounds to prostaglandins $E_2$ and $E_3$. In Flowsheet A, J is an appropriate blocking group for the hydroxy and carboxy functions in (VII) which is compatible with the conjugate addition reaction and also is ultimately removable by acid-catalyzed hydrolysis or other techniques which will not disrupt the sensitive 11-oxy-9-keto system in the products (XIII), (XV), (XVIII) and (XVII). Particularly useful for this purpose are the tetrahydropyranyl group and various trialkylsilyl groups; e.g., dimethylisopropylsilyl, trimethylsilyl, dimethyl-tert-butylsilyl, and the like. An alkyl ester, preferably methyl, of the carboxylic acid function is also embraced within this concept, since prostaglandin methyl esters are often useful per se for pharmaceutical applications and thus do not have to be removed. On the other hand, they can be hydrolyzed in a compatible manner by enzymatic procedures, for example, with Baker's yeast.

FLOWSHEET A

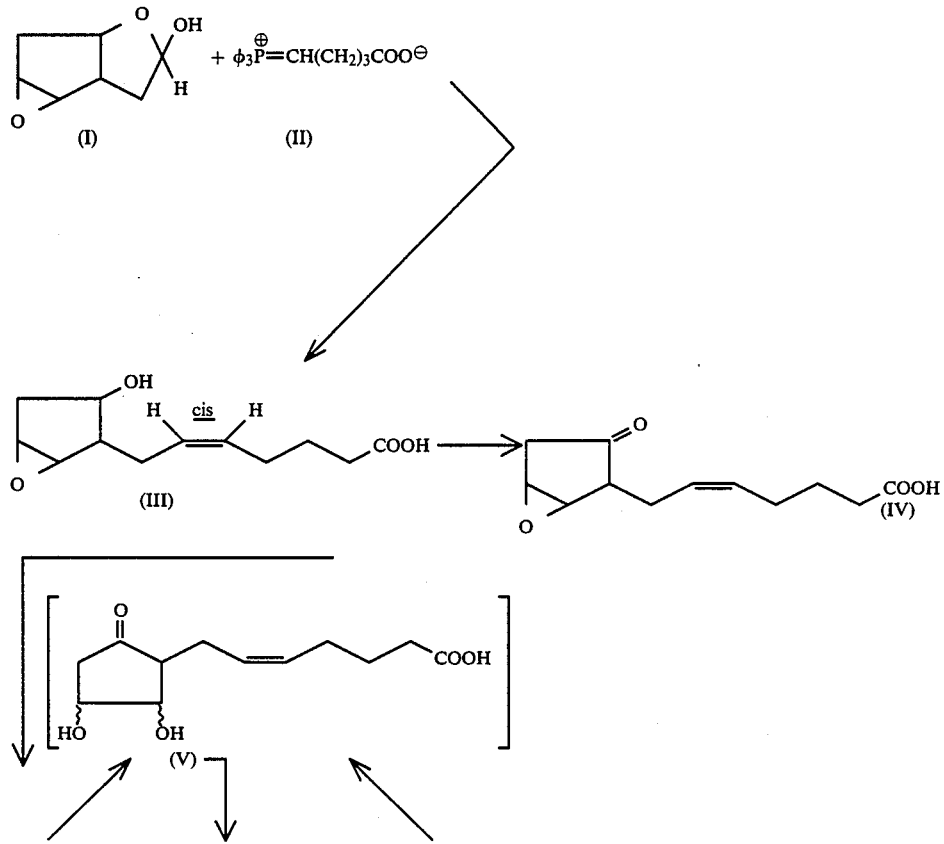

-continued
FLOWSHEET A
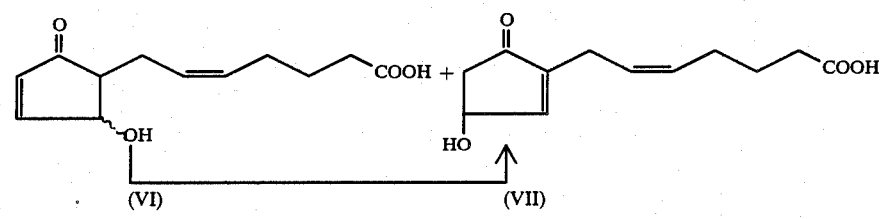
(VI)     (VII)
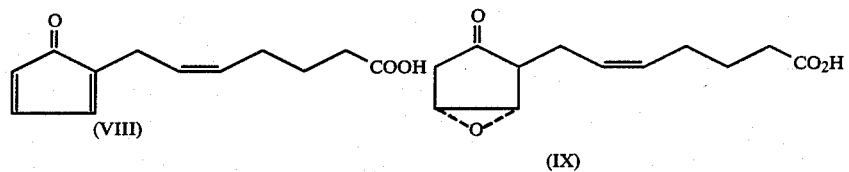
(VIII)     (IX)
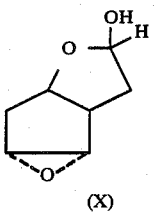
(X)
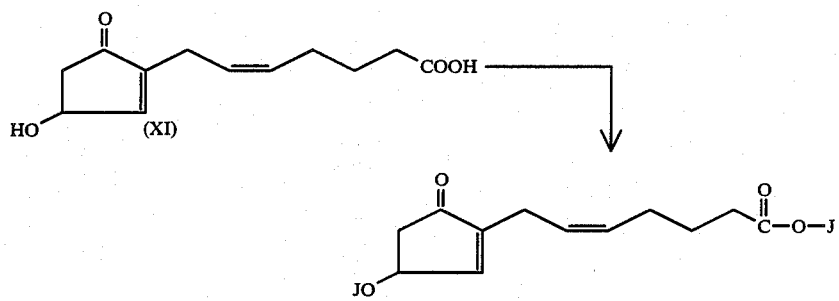
(XI)
(XII)
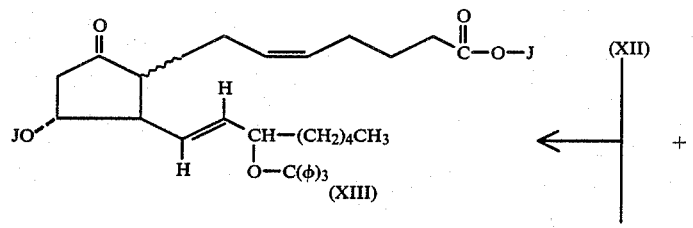
(XIII)
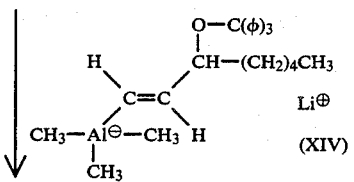
(XIV)
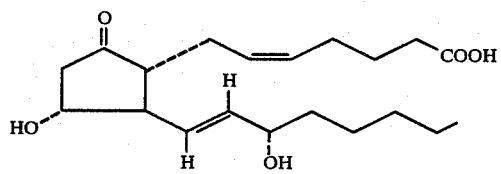
(XV, PGE$_2$)

-continued
FLOWSHEET A

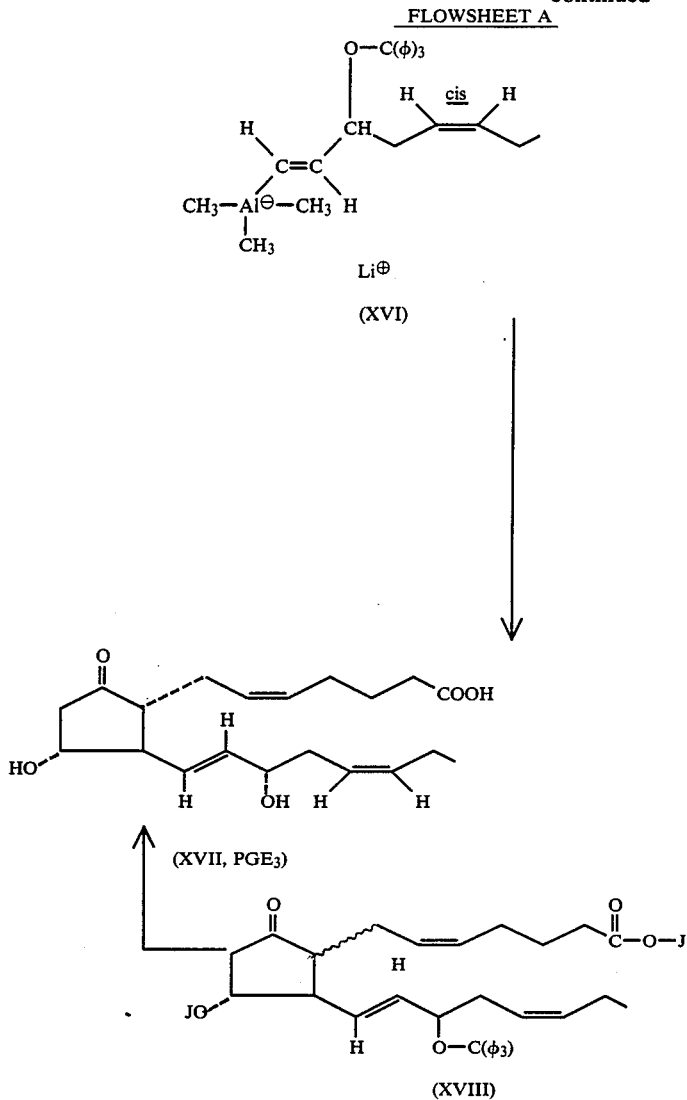

In accordance with the above reaction scheme the 3,4-epoxylactol (I) [E. J. Corey and R. Noyori, *Tetrahedron Letters*, 311 (1970)] is treated with the ylide (II) to give the 3,4-epoxycyclopentanol (III) bearing the α-chain of the prostaglandin 2 series. Oxidation (for example with $H_2CrO_4.H_2SO_4$-ether or Jones reagent) of (III) provides the epoxy ketone (IV), mild base treatment of which results in the initial formation of the 4-hydroxycyclopent-2-en-1-one (VII) and the isomeric 3-hydroxycyclopent-4-en-1-one (VI) as a mixture. Further treatment of this mixture with dilute base under mild conditions (preferably pH 10.3–10.6 for 24 hours) results in the isomerization of the 3-hydroxy isomer (VI) to the desired (VII). We believe that the transformation of the epoxy ketone (IV) to the hydroxycyclopentenones (VI) and (VII) and the isomerization of (VI) to (VII) may take place through the intermediacy of the 3,4-diol (V). It is also conceivable that isomerization of (VI) to (VII) procedes via the epoxy derivative (IV) or the corresponding α-epoxide (IX). Another possible intermediate for the isomerization of (VI) to (VII) is the corresponding diene (VIII). The preparation of (VII) is also possible via the α-epoxide series from (X) via the α-epoxides corresponding to (III) and (IV) such as (IX). In practice, it is most convenient to utilize a mixture of α- and β-epoxides (X and I).

The hydroxy and acid function in the 4-hydroxycyclopentenones (XI) are then appropriately blocked to give (XII). Appropriate blocking groups are tetrahydropyranyl, trimethylsilyl, dimethyl-isopropylsilyl, dimethyl-tert-butylsilyl and the like. The methyl ester can be prepared by just treating with diazomethane followed by blocking the 4-hydroxy group. Treatment of (XII) with the lithio alanate (XIV) or its equivalent gives the conjugate addition product (XIII) in which the configuration at $C_8$ is undetermined. Mild acid treatment, for example with acetic acid:tetrahydrofuran:water, (4:2:1), of (XIII) results in the removal of blocking groups, and if necessary equilibration to the all-trans configuration, to give prostaglandin $E_2$ (XV). Similarly treatment of (XII) with the lithio alanate (XVI) gives prostaglandin $E_3$ (XVII). See the appropriate examples hereinbelow and also our U.S. Pat. No. 3,873,607 for a detailed description of these conjugate addition techniques.

Substitution in Flowsheet A, of ylide (XIX), wherein p is as hereinabove defined, for the ylide (II) provides, by transformations analogous to those described in Flowsheet A [(I) to (XI) and (XII)], the 4-hydroxycyclopent-2-en-1-ones (XX) and their blocked ether-esters (XXI). These novel and useful intermediates are a part of the present invention.

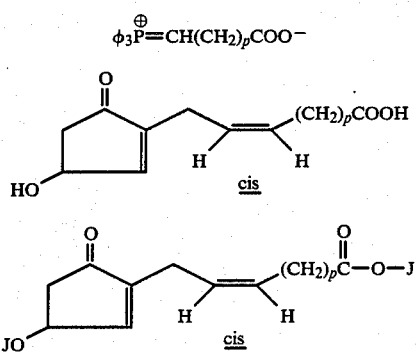

Conjugate addition of (XIV) or (XVI) as described hereinabove to (XXI) provides the corresponding homo and nor prostaglandins of the $E_2$ and $E_3$ series, respectively, 9-keto reduction of which by the methods well known in the art then furnishes the corresponding prostaglandins of the F series. For example, reduction with sodium borohydride gives separable mixtures of the F$\alpha$ and F$\beta$ derivatives and lithium perhydro-9b-boraphenalylhydride stereospecifically provides the F$\alpha$ derivatives. As is well-known, the E prostaglandins on mild treatment with mineral acid also can provide the corresponding prostaglandin of the A series. The prostaglandins derivable from (XXI) are useful substances in that they also show prostaglandin-like biological activity, often of a more selective nature which is of significant advantage.

The novel 4-oxycyclopentenones of this invention when prepared by the procedure described herein are obtained as optically inactive racemates. These racemates can be resolved into the component enantiomers (XXII) and (XXIII) by the usual procedures well established in the art.

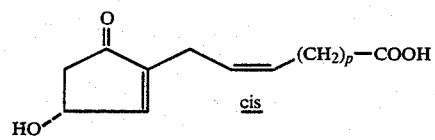

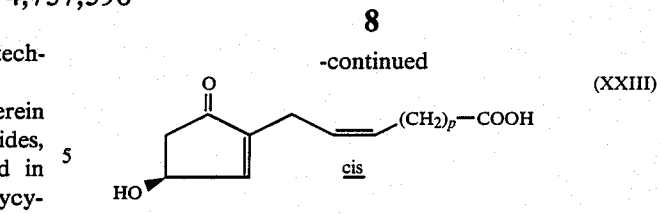

For example, the 4-hydroxycyclopentenone racemates may be resolved into their component enantiomers by derivatizing the ketone function with a reagent having an optically active center. The resulting diastereomeric mixtures can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride (to give (XXIX), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (XXII) and (XXIII). A useful procedure for the resolution of a 4-hydroxycyclopentenone racemate via an oxime such as (XXIV) is described in the art [R. Pappo, P. Collins and C. Jung, *Tetrahedron Letters*, 943 (1973)].

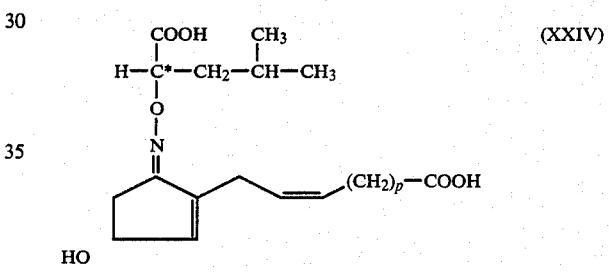

It is also possible to resolve the 4-hydroxycyclopentenone racemate (XXV) by microbiological means. Thus, treatment of the 4-O-alkanoyl or aroyl derivatives (XXVI R=aryl or alkyl) of racemate (XXV) (preferably the 4-O-acetyl and 4-O-propionyl derivatives) with an appropriate microorganism, preferably a Saccharomyces species e.g., 1375–143, affords preferential de-O-acylation of the 4-(R)-enantiomer to give enantiomer (XXII), which is then separated from the unreacted 4(S)-O-acyl enantiomer (XXVII) by chromatographic procedures. After separation, mild hydrolysis of the 4(S) derivative (XXVII) provides the 4(S)-hydroxycyclopentenone enantiomer (XXIII). [See N. J. Marsheck and M. Miyano, *Biochima et Biophysica Acta*, 316, 363 (1973) for related examples.]

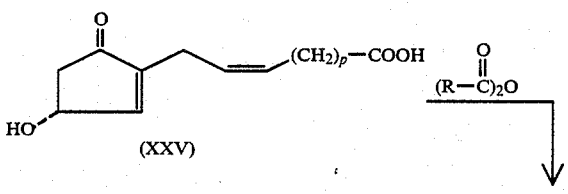

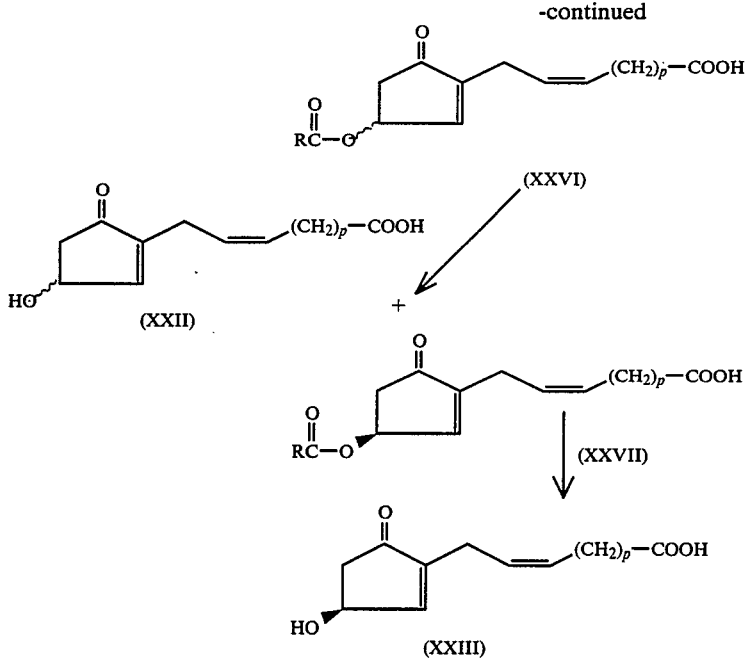

An alternative resolution procedure involves derivatization of the alcohol function of the racemic hydroxycyclopentenones (XXV) to give ester-acid derivatives such as (XXVIII) wherein n is zero or two.

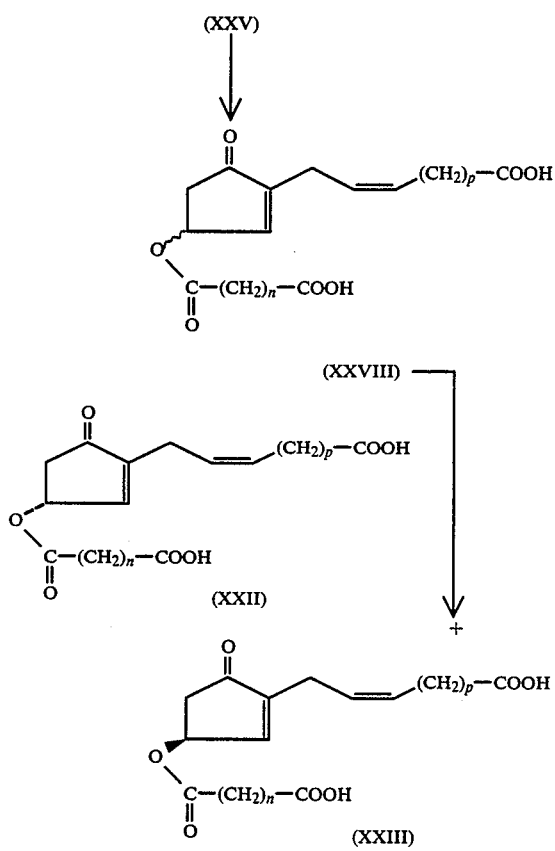

Derivatives such as (XXVIII) may be obtained from the corresponding free hydroxycyclopentenone (XXV) by treatment in the usual manner with oxalyl chloride, succinyl chloride, succinic anhydride and the like. Treatment of the resulting acid (XXVIII) with optically active amines e.g., 1-(−)- -methylbenzylamine, d-(+)- -methylbenzylamine, brucine, dehydroabietylamine, strychnine, quinine, cinchonine, quinidine ephedrine, (+)-α-amino-1-butanol and the like, and fractional recrystallization of the resulting diastereomeric mixtures, followed by cleavage of the 4-oxy ester function in each of the individually isolated diastereomers (XXIX) and (XXX) provides the individual 4(R)- and 4(S)-hydroxycyclopentenone enantiomers (XXII) and (XXIII), respectively. Cleavage of the oxalate acid esters (XXIX and XXX, n=0) can be accomplished by treatment with lead tetraacetate in pyridine solution. For an example of a similar use of oxalate acid-esters see J. G. Molotkovsky and L. D. Bergelson, *Tetrahedron Letters*, 4791 (No. 50, 1971); for an example of the use of a succinate acid-ester see B. Goffinet, Ger. Offen. No. 2,263,880; *Chem. Abstracts*, 79, $7815_z$ (1973).

The invention will be described in greater detail in conjunction with the following specific examples.

EXAMPLE 1

Preparation of 4-bromo-2-(6-carboxyhexyl)cyclopent-2-en-1-one

A stirred mixture of 35.9 g. (0.171 moles) of 2-(6-carboxyhexyl)cyclopent-2-en-1-one [Bagli et al., *Tetrahedron Letters*, No. 5, 465 (1966)], 35.0 g. (0.197 moles) of N-bromosuccinimide, and 600 ml. of carbon tetrachloride is refluxed for 35 minutes. The mixture is cooled to 5° C. and filtered. The filtrate is washed with cold water, dried over magnesium sulfate, and taken to dryness to give an oil, $\lambda max.^{MeOH} = 225$ mμ (8850); $\nu max. = 1705$ (carbonyl groups) and 1625. cm$^{-1}$ (olefin group).

EXAMPLE 2

Preparation of 2-(6-carboxyhexyl)-4-hydroxy-cyclopent-2-en-1-one

To a stirred solution of 10.6 g. (ca. 34 mmoles) of crude 4-bromo-2-(6-carboxyhexyl)cyclopent-2-en-1-one (Example 1) in 100 ml. of acetone and 65 ml. of water is added 8.80 g. (45.2 mmoles) of silver fluoborate during 2 minutes. The temperature is maintained at 25°–30° C. by external cooling. The mixture is stirred for 90 minutes, filtered, saturated with sodium chloride, and extracted with ether. The extract is extracted with half saturated sodium bicarbonate solutions. The basic solutions is reacidified with dilute hydrochloric acid, saturated with sodium chloride, and extracted with ether. The extract is washed with water and saturated sodium chloride solution, dried over magnesium sulfate, and concentrated. The crude product is purified by partition chromatography on Celite to give an oil; $\lambda max.^{MeOH}=233$ m$\mu$. (7360); $\nu max.=3380$ (hydroxyl groups), 1710 (carbonyl groups), and 1632 cm$^{-1}$ (olefin group).

EXAMPLE 3

Preparation of 4-tetrahydropyranyloxy-2-(6-tetrahydropyranylcarboxyhexyl)cyclopent-2-en-1-one To a stirred solution of 5.59 g. (24.6 mmoles) of 4-hydroxy-2-(6-carboxyhexyl)cyclopent-2-en-1-one (Example 2) and 20.7 g. (246 mmoles) of dihydropyran in 100 ml. of methylene chloride at 20° C. is added 47 mg. (0.246 mmoles) of p-toluenesulfonic acid monohydrate in one portion. The temperature is maintained at 20°–25° C. by cooling and is stirred for one hour at that temperature. The solution is diluted with 200 ml. of ether and poured into a mixture of 40 ml. of saturated sodium bicarbonate solution, 40 ml. of saturated sodium chloride solution, and 80 ml. of water. The phases are separated, and the aqueous phase is extracted with additional ether. The total extract is washed successively with water and saturated sodium chloride solution, dried over potassium carbonate, and freed of volatile matter by concentration at reduced pressure to give an oil, $\lambda max.^{MeOH}=223$ m$\mu$ (9500); $\nu max.$ 1730 (ester carbonyl group), 1705 (ketone carbonyl group), and 1030 cm$^{-1}$ (tetrahydropyranyloxy groups).

EXAMPLE 4

Preparation of 2-carbalkoxy(methyl/ethyl)-2-(4-carbethoxybutyl)cyclopentan-1-one To a stirred solution of the sodium cyclopentanone carboxylate enolate in dimethoxyethane, prepared from 187 g. (1.248 moles) of 2-cyclopentanone carboxylate (mixed methyl and ethyl esters), 52.4 g. (1.248 moles) sodium hydride (57.2% in mineral oil) and 1.6 l. of dimethoxyethane, is added dropwise 309 g. (1.212 moles) of ethyl 5-iodovalerate. The reaction mixture is stirred and heated at reflux for 18 hours. The mixture is cooled and filtered. The solvent is removed from the filtrate by evaporation and the residue is poured into dilute hydrochloric acid and extracted with ehter. The combined extracts are washed with water and saline, dried over magnesium sulfate and evaporated to give an oil. The oil is distilled under reduced pressure to give 274 g. of a light yellow oil, b.p. 140°–143° C. (0.17 mm).

EXAMPLE 5

Preparation of 2-(4-carboxybutyl)cyclopentan-1-one

A stirred mixture of 274 g. of 2-carbalkoxy (mixed methyl and ethyl esters)-2-(4-carbethoxybutyl)cyclopentan-1-one (Example 4), 600 ml. of 20% hydrochloric acid and 325 ml. of acetic acid is heated at reflux for 20 hours. Solution occurs in approximately ½ hour. The solution is cooled and diluted with water and extracted with ether. The combined extracts are washed with saline and dried over magnesium sulfate and evaporated. The residue is evaporated twice with toluene to give 144 g. of an oil.

EXAMPLE 6

Preparation of 2-(4-carbethoxybutyl)cyclopentan-1-one

A stirred solution of 124 g. (0.673 mole) of 2-(4-carboxybutyl)cyclopentan-1-one (Example 5), 800 ml. of ethanol and 1 g. of p-toluenesulfonic acid monohydrate is heated at reflux for 18 hours. The solvent is evaporated and the residue is dissolved in ether. The ether solution is washed with saline, diluted sodium bicarbonate solution and again with saline, dried over magnesium sulfate and evaporated. The oil is distilled under reduced pressure to give 149 g. of a colorless oil, b.p. 106°–109° C. (0.23 mm).

EXAMPLE 7

Preparation of ethyl and methyl 2-(6-carbethoxyhexyl)-1-cyclopentanon-2-carboxylate In the manner described in Example 4, ethyl and methyl 2-cyclopentanone carboxylate is reacted with ethyl 7-bromoheptano ate to furnish the subject product, b.p. 147° C. (0.09 mm).

EXAMPLE 8

Preparation of 2-(6-carboxyhexyl)cyclopentan-1-one

In the manner described in Example 5, ethyl and methyl 2-(6-carbethoxyhexyl)-1-cyclopentanone-2-carboxylate (Example 7) is hydrolyzed to furnish the subject product, b.p. 143° C. (0.05 mm).

EXAMPLE 9

Preparation of 2-(6-carbethoxyhexyl)cyclopentan-1-one

In the manner described in Example 6, 2-(6-carboxyhexyl)cyclopentan-1-one (Example 8) is esterified to furnish the subject product, b.p. 110° C. (0.03 mm).

EXAMPLE 10

Preparation of 1-acetoxy-2-(6-carbethoxyhexyl)cyclopent-1-ene

A stirred solution of 100 g. of 2-(6-carbethoxyhexyl)cyclopentan-1-one (Example 9) in 250 ml. of acetic anhydride containing 0.940 g. of p-toluenesulfonic acid monohydrate is heated to boiling under partial reflux allowing distillate at 118° C. or less (i.e., acetic acid) to escape through a Vigreaux column equipped with a condenser to collect the distillate. After 16 hours, during which period acetic anhydride is added in portions in order to keep the solvent level at at least 100 ml., the solution is cooled and poured cautiously into a stirred cold mixture of saturated sodium bicarbonate solution (400 ml.) and hexane (250 ml.). The resulting mixture is stirred for an additional 30 minutes during which period solid sodium bicarbonate is added periodically to insure a basic solution. The hexane layer is separated and washed with saturated sodium chloride solution, dried with anhydrous magnesium sulfate and taken to dryness. Distillation of the residual oil gives 102 g. (87%) of pale yellow oil, b.p. 118° C. (0.07 mm).

EXAMPLE 11

Preparation of 2-(6-carbethoxyhexyl)cyclopent-2-en-1-one

To a rapidly stirred mixture of 50 g. of 1-acetoxy-2-(6-carbethoxyhexyl)cyclopent-1-ene (Example 10) in 150 ml. of chloroform, 200 ml. of water and 18.8 g. of calcium carbonate, cooled in an ice bath, is added dropwise over a period of about 30 minutes, a solution of 30 g. of bromine in 50 ml. of carbon tetrachloride. After stirring for an additional 45 minutes the chloroform layer is separated and washed successively with dilute sodium thiosulfate solution, saturated sodium chloride solution, dried with anhydrous magnesium sulfate and taken to dryness under reduced pressure.

The residual oil is dissolved in 50 ml. of N,N-dimethylformamide and added to a mixture of 33 g. of lithium bromide and 32 g. of lithium carbonate in 375 ml. of N,N-dimethylformamide, previously dried by refluxing with 375 ml. of benzene under a Dean-Stark apparatus followed by distillation of the benzene. The mixture is stirred at the reflux temperature for 30 minutes, then cooled and poured into 850 ml. of ice-cold water The resulting mixture is acidified (cautiously) with 4N hydrochloric acid and extracted with ether three times. The combined ether extracts are washed with saturated sodium chloride solution, dried with anhydrous magnesium sulfate and taken to dryness under reduced pressure to afford 41.5 g. of an amber oil. In order to convert any isomeric material to the desired product, 41.5 g. of the above material is treated with 0.500 g. of p-toluenesulfonic acid monohydrate in 450 ml. of absolute alcohol at the reflux temperature for 18 hours. The solution is taken to dryness under reduced pressure. The resulting gum is dissolved in ether and washed with saturated sodium bicarbonate solution, saturated sodium chloride solution, dried with anhydrous magnesium sulfate and taken to dryness under reduced pressure. The residual oil is distilled to give 30.2 g. of product; b.p. 118° C. (0.05 mm); $\lambda_{max}^{MeOH}$ 229 m$\mu$ ($\epsilon$9950); $\lambda_{max}$ 5.75, 5.85, 6.15, 8.45$\mu$; vapor phase chromatography shows 99% product, containing 1% 2-(6-carbethoxyhexyl)cyclopentane-1-one.

This product can be purified by the following procedure. A mixture of 120 g. of 2-(6-carbethoxyhexyl)-2-cyclopentenone, containing approximately 5% of the saturated analogue, and 7.67 g (10 mole percent) of p-carboxyphenylhydrazine in 400 ml. of absolute ethanol is stirred at ambient temperatures for 18 hours and is then refluxed for 1 hour. The mixture is cooled, the solvent is evaporated, and the residue is taken up into 150 ml. of chloroform and passed through a column of 450 g. of aluminum oxide (Merck). The filtrate is evaporated to yield a colorless oil containing <0.5% of the saturated impurity.

EXAMPLE 12

Preparation of 2-(6-carbomethoxyhexyl)cyclopent-2-en-1-one

A solution of 50 g. of 2-(6-carboxyhexyl)cyclopent-2-en-1-one [Bagli et al., *Tetrahedron Letters*, No. 5, 465 (1966)] in 1400 ml. of methanol containing 2.7 g. of p-toluenesulfonic acid monohydrate is allowed to stand at room temperature in a stoppered flask for about 24 hours. The solution is taken to dryness. The residue is taken up in ether and the etheral solution is washed several times with saline solution, dried with anhydrous magnesium sulfate, and taken to dryness to afford the subject methyl ester.

EXAMPLE 13

Preparation of 3-triphenylmethoxy-1-octyne

A mixture of 1.26 g. (10.0 mmoles) of 1-octyn-3-ol, 4.85 g. (15.0 mmoles) of triphenylmethyl bromide, and 50 ml. of dry pyridine is heated at 95° C. for 60 minutes with occasional swirling. The solution is cooled, treated with water, and extracted with ether. The extract is washed successively with water and saturated sodium chloride solution, dried over magnesium sulfate, and concentrated. The crude product is purified by chromatography on Florisil and recrysallization from petroleum ether to give white crystals, m.p. 65°–66.5°, $v$max. (KBr) 3280 (acetylenic hydrogen), 1605, 1030, and 702 cm$^{-1}$ (triphenylmethoxy group).

EXAMPLE 14

Preparation of ethyl 9-oxo-15-triphenylmethoxy-13-trans-8$\xi$-prostenoate

A stirred solution of 7.37 g. (20.0 mmoles) of 3-triphenylmethoxy-1-octyne (Example 13) in 10 ml. of benzene is treated with 16.7 mg. of 1.2M diisobutylaluminum hydride in hexane, and the resulting solution is heated at 50° C. for 2 hours. The solution is cooled to 0° C. and treated with 10.5 ml. of 1.7M methyl lithium in ether. After stirring for a 20 minute period at ambient temperature, the alanate solution is cooled to 0° C. and treated with a solution of 3.98 g. (16.7 mmoles) of 2-(6-carbethoxyhexyl)cyclopent-2-en-1-one (Example 11) in 5 ml. of ether. The resulting solution is stirred at ambient temperature for 22.5 hours, diluted with ether, and poured into a stirred mixture 2N acetic acid and ice. After stirring until methane evolution ceases, the orgnaic phase is separated and washed successively with water and saturated sodium chloride solution. The extract is dried over magnesium sulfate and concentrated. The crude product in the residue is purified by chromatography on silica gel to give an oil, $v$max. 1735 (carbonyl groups), 967 (trans vinyl group), and 705 cm$^{-1}$ (triphenylmethoxy group).

EXAMPLE 15

Preparation of ethyl 15-hydroxy-9-oxo-13-trans-prostenoate

A 0.05M solution of ethyl 9-oxo-15-triphenylmethoxy-13-trans-8ξ-prostenoate (Example 120) in glacial acetic acid-tetrahydrofuran-water (4:2:1) is heated at 45° C. for 3.5 hours. The solvents are evaporated at reduced pressure, and the residue is dissolved in ether. The solution is washed successively with water, 0.5N sodium bicarbonate solution, and saturated sodium chloride solution; dried over magnesium sulfate; and concentrated Column chromatography of the crude product on silica gel gives two epimeric substances which are purified separately by thin layer chromatography to give oils differing only in chromatographic behavior, $\nu$max. 3470 (hydroxyl group), 1735 (carbonyl groups), and 967 cm$^{-1}$ (trans vinyl group).

EXAMPLE 16

Preparation of tetrahydrpyran-2-yl 9-oxo-11-tetrahydropyranyloxy-15-triphenylmethoxy-13-trans-8ξ-prostenoate In the manner described in Example 14, 13.6 g. (37 mmoles) of 3-triphenylmethoxy-1-octyne (Example 13) contained in 18.5 ml. of benzene is converted to an alanate reagent by treatment with 31 ml. of 1-2M diisobutylaluminum hydride in hexane and 21 ml. of 1.7M methyl lithium in ether. To the stirred, ice-cold reagent is added a solution of 10.97 g. (24.6 mmoles) of 2-(6-tetrahydropyranylcarboxyhexyl)-4-tetrahydropyranyloxycyclopent-2-en-1-one (Example 3) in 10 ml. of ether during 10 minutes. The resulting solution is stirred at ambient temperature for 20 hours, diluted with ether, and poured into a stirred mixture of 2N hydrochloric acid and ice. The organic phase is separated and washed successively with water and saturated sodium chloride solution. The extract is dried over magnesium sulfate, and the solvents are evaporated at reduced pressure to give the crude product as an oil, $\nu$max. 1735 (carbonyl groups), 1030 (tetrahydropyranyloxy groups), 970 (trans vinyl group), and 705 cm$^{-1}$ (triphenylmethoxy group).

EXAMPLE 17

Preparation of 11,15-dihydroxy-9-oxo-13-trans-prostenoic acids

A 0.05M solution of crude tetrahydropyran-2-yl 9-oxo-11-tetrahydropyranyloxy-15-triphenylmethoxy-13-trans-prostenoate (Example 16) in glacial acetic acid-tetrahydrofuran-water (4:2:1) is heated at 45° C. for 3.5 hours. The solution is dilute with water and extracted with ether. The extract is washed successively with water and saturated sodium chloride solution and dried over magnesium sulfate. The solvents are removed at reduced pressure. Column chromatography of the residue on acid-washed silica gel gives the title compounds as a pair of epimeric substances which are purified separately by partition chromatography.

The fast-running epimer (15-epi-d,l-prostaglandin E$_1$) is obtained as an oil, $\nu$max. 1735 (ketone carbonyl group), 1710 (acid carbonyl group), and 967 cm$^{-1}$ (trans vinyl group); NMR (acetone-d$_6$) 5.68 (multiplet, vinyl hydrogens) and 4.11S(multiplet, carbinolic hydrogens).

The slow-running epimer (d,l-prostaglandin E$_1$) is recrystallized from ethyl acetate-petroleum ether to give white crystals, m.p. 100°–105° C., $\nu$max, (KBr) 1725 (ketone carbonyl group), 1700 (acid carbonyl group), and 970 cm$^{-1}$ (trans vinyl group); NMR (acetone-d$_6$) 5.67 (multiplet, vinyl hydrogens) and 4.12 (multiplet, carbinolic hydrogens).

EXAMPLE 18

Preparation of 1-chloro-trans-1-octen-3-one

To a slurry of 233.5 g. (1.75 moles) of aluminum chloride in 390 ml. of carbon tetrachloride, saturated with acetylene and cooled in an ice bath, is added over 20 minutes 201.9 g. (1.50 moles) of hexanoyl chloride. After the addition is complete, acetylene is bubbled into the mixture as rapidly as it is absorbed and for 1 hour after absorption becomes slow. The mixture is poured onto 1700 g. of ice and 720 ml. of saturated brine. The organic phase is separated and the aqueous phase is washed with ether. The combined organic phase and washings are washed with saturated brine, dried (Na$_2$SO$_4$) and evaporated. The residual oil is combined with 10 g. of hydroquinone and distilled to yield a colorless oil, b.p. 51°–52° C. (0.10 torr).

EXAMPLE 19

Preparation of 1-iodo-trans-1-octen-3-one

A mixture of 54.5 g (0.364 mole) of sodium iodide and 40 g. (0.249 mole) of 1-chloro-trans-1-octen 3-one (Example 18) in 360 ml. of acetone is stirred and refluxed for 24 hours. The reaction mixture is cooled, filtered and concentrated. The residue is partitioned between water and ether. The organic phase is washed with dilute sodium bicarbonate solution, brine, dried (MgSO$_4$) and evaporated to an oil. This material is used directly without purification.

EXAMPLE 20

Preparation of 1-bromo-trans-1-octen-3-one

A mixture of 68.0 g. (0.424 mole) of 1-chloro-trans-1-octen-3-one (Example 18) and 444 g. (4.24 moles) of anhydrous lithium bromide in 900 ml. of 2-pentanone is refluxed for 30 minutes, cooled, and partitioned between ice water and ether. The organic phase is washed with water and saturated brine, dried (NaSO$_4$), and evaporated to an oil. This material is used directly without purification.

EXAMPLE 21

Preparation of 1-bromo-trans-1-octen-3-ol

To an ice cooled mixture of 14.29 g. (0.378 mole) of sodium borohydride in 400 ml. of anhydrous ethanol is added the crude 1-bromo-trans-1-octen-3-one (Example 20, from 0.424 mole of 1-chloro-trans-1-octen-3-one) over 30 minutes. The mixture is stirred for 2 hours with ice cooling and is then partitioned between ice water and benzene. The organic phase is washed with water and saturated brine, dried (Na$_2$SO$_4$), and evaporated to an oil. Fractional distillation yields the title compound as a colorless oil, b.p. 66°–68° C. (0.025 torr).

EXAMPLE 22

Preparation of 1-bromo-3-triphenylmethoxy-trans-1-octen

A mixture of 6.212 g. (0.030 mole) of 1-bromo-trans-1-octen-3-ol (Example 21) and 10.67 g. (0.033 mole) of triphenylmethyl bromide in 40 ml. of pyridine is heated to 100° C. for 1.5 hours under an inert atmosphere. The mixture is cooled and filtered. The filtrate is partitioned between ice water and ether. The organic phase is washed with cold dilute hydrochloric acid, saturated sodium bicarbonate solution, and saturated brine, dried ($NaSO_4$), and evaporated to an oil. The latter is dissolved in hexane and passed through 250 g. of Florisil ® to yield after evaporation a colorless oil. Found for $C_{27}H_{29}OBr$: C, 72.13, H, 6.61; Br, 17.57.

EXAMPLE 23

Preparation of 1-iodo-trans-1-octen-3-ol

Treatment of 63 g. (0.25 mole) of 1-iodo-trans-1-octen-3-one (Example 19) with sodium borohydride in the manner described in Example 21 gave 58 g. of yellow oil. The oil is purified by adsorption chromatography on a magnesia silica gel column using benzene as eluent to give a light yellow oil.

EXAMPLE 24

Preparation of 1-iodo-3-triphenylmethoxy-trans-1-octene

Treatment of 7.62 g. (0.03 mole) of 1-iodo-trans-1-octen-3-ol (Example 23) with 10.67 g. (0.033 mole) of triphenylmethyl bromide in pyridine in the manner described in Example 22 gave 13.448 g. (90%) of a colorless oil.

EXAMPLE 25

Preparation of 11-deoxy-prostaglandin-$E_1$ methyl ester and methyl 15-hydroxy-9-oxo-13-cis-prostenoate To a slurry of 0.535 g. (0.022 g. atom) of magnesium in 6 ml. of tetrahydrofuran is added under an inert atmosphere 2 ml. of a solution of 6.548 g. (0.01455 mole) of 1-bromo-3-trityloxy-trans-1-octene (Example 22) in 8 ml. of tetrahydrofuran. Reaction is initiated by warming the mixture to 45° C. and adding 1 drop of methyl iodide. The remainder of the halide is added at a rate to maintain a temperature of 43°–46° C. and the mixture is heated at 45° C. for 1 hour after complete addition of the halide. The Grignard reagent is cooled and added to an ice cooled solution of 2.615 g. (0.0117 mole) of 2-(6-carbomethoxyhexyl) 2-cyclopentenone (Example 12) and 0.229 g. of copper (I) iodide-tri-n-butylphosphine in 6 ml. of ether over 6 minutes. The mixture is stirred with ice cooling for 30 minutes and poured into 200 ml. of saturated ammonium chloride. The mixture is extracted into ether and the organic phase is washed with water and saturated brine, dried ($NaSO_4$) and evaporated. The residual oil is heated to 80° C. for 30 minutes with 80% aqueous acetic acid under an inert atmosphere. This mixture is cooled, evaporated to dryness, and the residue is separated by dry column chromatography on silica gel using benzene-ethyl acetate 4:1 as eluent. The title compounds are isolated as oils with Δ13 trans/Δ13 cis in ratio of 10:1. Complete resolution is effected with partition chromatography [for a description see M. J. Weiss et al., *Tetrahedron*, 20, 357 (1964)] on acid-washed Celite -545 using heptane:acetonitrile (Hold Back Volume=1000 ml.); 11-deoxy-prostaglandin-$E_1$ methyl ester is obtained in Hold Back Volume 3–5 and methyl 15-hydroxy-9-oxo-13-cis-prostenoate is obtained in Hold Back Volume 6–8.

EXAMPLE 26

Preparation of 11-deoxy-prostaglandin-$E_1$ methyl ester and methyl 15-hydroxy-9-oxo-13-cis-prostenoate To a slurry of 0.243 g. (0.010 g. atom) of magnesium in 4 ml. of tetrahydrofuran is added under an inert atmosphere 2 ml. of a solution of 4.494 g. (0.010 mole) of 1-bromo-3-trityloxy-trans-1-octene in 4 ml. of tetrahydrofuran. Reaction is initiated by warming the mixture to 65° C. and adding 1 drop of methyl iodide. The remainder of the halide is added at a rate to maintain a temperature of 65°–70° C. and the mixture is heated at 75°–80° C. for 30 minutes after complete addition of the halide. The Grignard reagent is cooled and added to 2.243 g. (0.010 mole) of 2-(6-carbomethoxyhexyl)-2-cyclopentenone and 0.200 g. of copper (I) iodide-tri-n-butylphosphine in 6 ml. of ether and worked up with saturated ammonium chloride solution and aqueous acetic acid in the manner of Example 15. The products are isolated as described in Example 25 to yield 11-deoxy-prostaglandin $E_1$ methyl ester and methyl 15-hydroxy-9-oxo-13-cis-prostenoate in a ratio of 2:1.

EXAMPLE 27

Preparation of Prostaglandin-$E_1$ and 9-oxo-11α,15-dihydroxy-13-cis-prostenoic acid A Grignard reagent is prepared as described in Example 25 from 0.535 g. (0.022 g. atom) of magnesium, 6.742 g. (0.015 mole) of 1-bromo-3-triphenylmethoxy-trans-1-octene (Example 22), and 11 ml. of tetrahydrofuran at a temperature of 40°–42° C. The Grignard reagent is added to 3.95 g. of 2-(6-carbotetrahydropyranyloxyhexyl)-4-tetrahydropyranyloxy-2-cyclopentenone (Example 3) and 0.589 g. of copper (I) iodide tri-n-butylphosphine in 10 ml. of tetrahydrofuran and is worked up with ammonium chloride as described in Example 25. The protecting groups are removed by treating the worked up material, as described in Example 16, with 320 mol of acetic acid-water-tetrahydrofuran 2:1:1 at 45° C. and the products are isolated by chromatography on silica gel with a benzene-ethyl acetate gradient and resolved via partition chromatography on acid-washed Celite 545.

EXAMPLE 28

Preparation of Prostaglandin-$E_1$, and 9-oxo-1α,15-dihydroxy-13-cis-prostenoic acid Treatment of 2-(6-carbotetrahydropyranylhexyl)-4-tetrahydropyranyloxy-2-cyclopentenone (Example 3) with the Grignard reagent prepared from 1-bromo-3-triphenylmethoxy-trans-1-octene (Example 22) in the presence of Copper (I) iodide tri-n-butylphosphine complex by the procedure described in Example 26 is productive of the subject compounds.

EXAMPLE 29

Preparation of 9α,15-dihydroxy-13-trans-prostenoic acid

To a solution of 433 mg. of 9-oxo-15-hydroxy-13-trans-prostenoic acid in 4.5 ml. of tetrahydrofuran, stirred in an ice bath under nitrogen atmosphere, is added dropwise 3.7 ml. of 0.76M lithium perhydro-9b-boraphenalylhydride. After 40 minutes at 0° C. there is added 1.62 ml. of 3N sodium hydroxide followed by 1.62 ml. of 30% hydrogen peroxide. Ether is added and the resulting solution is acidified with 2N hydrochloric acid. The ether layer is washed several times with saturated sodium chloride solution, dried with anhydrous magnesium sulfate and taken to dryness to give the subject product as an oil.

EXAMPLE 30

Preparation of 1-iodo-3-(p-anisyldiphenylmethoxy)-trans-1-octene

A mixture of 14.92 g. (0.0588 mole) of 1-iodo-trans-1-octen-3-ol (Example 74) and 18.2 g. (0.0588 mole) of p-anisyldiphenylmethyl chloride in 165 ml. of dry pyridine is heated at 60° C. for 18 hours under an inert atmosphere. The mixture is cooled and the solvent is evaporated in vacuo. The residue is partitioned between ether and water, and the organic phase is washed with water and saturated brine, dried ($MgSO_4$), and evaporated. The residue is chromatographed upon 300 g. of Florisil ® packed in hexane and the product is eluted with hexane and 4:1 hexane-benzene the yield and colorless oil.

EXAMPLE 31

Preparation of methyl esters of
dl-11-deoxyprostaglandin-$E_1$ and
dl-11-deoxy-15-epi-prostaglandin $E_1$ To a solution of 6.030 g. (0.01215 mole) of 1-iodo-3-triphenylmethoxy-trans-1-octene (Example 24) in 8 ml. of toluene cooled to −78° C. under an inert atmosphere is added 5.2 ml. of a 2.3M solution of n-butyllithium in hexane. The resulting solution is allowed to warm to −40° C. and is maintained at this temperaure for 1 hour. To the solution containing 3-triphenylmethoxy-trans-1-octenyl lithium is then added 5.0 ml. of a 2.44M (0.0122 mole) solution of trimethylaluminum in heptane and the mixture is allowed to warm to −10° C. The mixture containing lithium trimethyl(3-triphenylmethoxy-trans-1-octenyl)alanate is then cooled to −78° C. and to it is added a solution of 2.725 g. (0.01215 mole) of 2-(6-carbomethoxyhexyl)-2-cyclopentenone (Example 12) dissolved in 10 ml. of diethyl ether. The mixture is allowed to warm to room temperature and is stirred at ambient temperature for 18 hours. The mixture is then poured onto ice and diluted hydrochloric acid and is extracted into ether. The organic phase is washed with water and saturated brine, dried ($Na_2SO_4$), and evaporated to yield a colorless oil. This oil is heated with 100 ml. of 80% aqueous acetic acid at 80° C. for 1 hour under an inert atmosphere. The resulting mixture is cooled and evaporated in vacuo to dryness with 100 ml. of xylene to yield and oil. This oil is dry-column-chromatographed upon 400 g. of silica gel using 4:1 benzene-ethyl acetate as eluent to yield a total of 2.59 g. of dl-11-deoxyprostaglandin $E_1$ and dl-11-deoxy-15-epi-prostaglandin $E_1$ methyl esters.

EXAMPLE 32

Preparation of
4-(trimethylsiloxy)-2-(6-carbotrimethylsiloxyhexyl)cyclopent-2-en-1-one To a solution of 5 g. of 2-(6-carbohexyl)-4-hydroxycyclopent-2-en-1-one (Example 2) in 10 ml. of dry N,N-dimethylformamide is added 5.4 g. of trimethylsilyl chloride in a nitrogen atmosphere. To the resulting solution cooled in a tap water bath is added 5.05 g. of trimethylamine in 10 ml. of N,N-dimentylformamide dropwise. The resulting mixture is stirred at 60° C. in an oil-bath for 2 hours, then at ambient temperatures for 18 hours. Triethylamine hydrochloride is removed by filtration and the filtrate is taken to dryness. The residual oil is distilled to give 2.6 g. of product, b.p. 156°–157° C. (0.07 mm.).

EXAMPLE 33

Preparation of
4-(dimethylisopropylsiloxy)-2-(6-carbodimethylisopropylsiloxyhexyl)cyclopent-2-en-1-one Treatment of 1 g. of 2-(6-carboxyhexyl)-4-hydroxycyclopent-2-en-1-one in 2 ml. of dry N,N-dimethylformamide containing 1.81 g. of dimethylisopropylsilyl chloride [E. J. Corey, R. K. Varma, *J. Amer. Chem. Soc.*, 93, 7320 (1971)] 157 g. of triethylamine in 2 ml. of N,N-dimethylformamide in the manner described in Example 32 gives 1.45 g. of product after two evaporations with toluene.

EXAMPLE 34

Preparation of
4-(dimethyl-t-butylsiloxy)-2-6-carbodimethyl-t-butylsiloxyhexyl)cyclopent-2-en-1-one To a 0° C. solution of 2.0 gm. (8.55 mole) 4-hydroxy-2-(6-carboxyhexylcyclopent-2-en-1-one (Example 2) and 3.65 gm. (54 mole) of imidazole in 5 ml. of dimethylformamide is added a slurry consisting of 4.07 gm. (27 mole) of dimethyl-t-butyl-chlorosilane in 5 ml. of dimethylformamide. The slurry is rinsed in with an additional 1 ml. of dimethylformamide. The ice-bath is removed and the solution is stirred at 37° C. for four hours. The solution is then poured into 140 ml. of water and the aqueous solution is extracted twice with 70 ml. of isomeric hexanes. The organic layers are combined, dried with magnesium sulfate and concentrated in vacuo to an oil. Toluene (50 ml.) is added twice and evaporated in vacuo to remove unwanted low boiling impurities.

The residue is maintained under active vacuum overnight to give 3.38 gm. (7.45 mole) of an oil, that shows no hydroxyl or carboxyl absorption in the infrared. $\bar{v}$max: 1720 $cm^{-1}$ (unsaturated ketone and silyl ester), 840, 815, 795, 780 $cm^{-1}$ (silyl ether and silyl ester).

EXAMPLE 35

Preparation of dl-prostaglandin $E_1$ and dl-epi-prostaglandin $E_1$

To a solution of 4.790 g. (0.0091 mole) of 3-(p-anisyldiphenylmethoxy)-trans-1-iodo-1-octene (Example 30) in 5 ml. of toluene cooled to $-78°$ C. under an inert atmosphere is added 3.9 ml. of 2.34M n-butyllithium in hexane. The resulting solution is warmed to $-40°$ C. and is maintained at this temperature for 1 hour. To the solution containing 3-(p-anisyldiphenylmethoxy)-trans-1-octenyllithium is then added 3.6 ml. of a 2.44M solution of trimethylaluminum in heptane and the mixture is allowed to warm to $0°$ C. The solution containing lithium trimethyl[3-(p-anisyldiphenylmethoxy)-trans-1-octenyl]alanate is then added to a solution of 3.30 g. (0.00726 mole) of 2-(6-carbo-t-butyldimethylsiloxyhexyl)-4-(t-butyldimethylsiloxy)-2-cyclopentenone (Example 34 dissolved in 10 ml. of ether cooled to $-45°$ C. under an inert atmosphere. The resulting solution is allowed to warm to room temperature and is stirred at ambient temperatures for 17 hours. The solution is then poured onto a mixture of 5 ml. of concentrated hydrochloric acid and 150 g. of ice. This mixture is stirred until the ice melts and is extracted into ether. The organic phase is washed with ice cold water and cold saturated brine, dired ($Na_2SO_4$), and is evaporated ($<37°$ C.) in vacuo. The resulting oil is then heated to $38°$ C. for 23 hours under an inert atmosphere with 100 ml. of 3:1:1 (V:V:V) acetic acid-tetrahydrofuran-water. The mixture is then evaporated with 150 ml. of xylene in vacuo ($<38°$ C.) to yield an oil. Chromatography of this oil upon 115 g. of Silic AR CC-4 (mallinckrodt) using a benzene-ethyl acetate gradient as eluent yields dl-prostaglandin $E_1$, m.p. 108-112 (from ethyl acetate) and dl-15-epi-prostaglandin $E_1$.

EXAMPLE 36

Preparation of 3-triphenylmethoxy-trans-1-octenyllithium

To a solution of 4.96 g. of 1-iodo-3-triphenylmethoxy-trans-1-octene (Example 24) in 10 ml. of toluene cooled to $-78°$ C. is added under an inert atmosphere 1 molar equivalent of n-butyllithium dissolved in hexane. The reaction muxture is allowed to warm to $-40°$ C. and is then maintained at that temperature for 1 hour to yield a hydrocarbon solution of 3-triphenylmethoxy-trans-1-octenyllithium.

EXAMPLE 37

Preparation of 3-(p-anisyldiphenylmethoxy)-trans-1-octenyllithium

To a solution of 5.26 g. of 1-iodo-3-(p-anisyldiphenylmethoxy)-trans-1-octene (Example 30) in 10 ml. of toluene, cooled to $-78°$ C., is added under an inert atmosphere 1 molar equivalent of n-butyllithium dissolved in hexane. The reaction mixture is allowed to warm to $-40°$ C. and is maintained at that temperature for 1 hour to yield a hydrocarbon solution of 3-(p-anisyldiphenylmethoxy)-trans-1-octenyllithium.

EXAMPLE 38

Preparation of all cis-2-(6-carboxy-2-cis-hexenyl)-3,4-oxidocyclopentanol

A solution of 1.42 g. (10.0 moles) of all-cis-5-hydroxy-2,3-oxidocyclopentylacetaldehyde-$\gamma$-lactol (E. J. Corey and R. Noyori, Tetrahedron Letters, 1970, 311) in 5 ml. of DMSO is added to a stirred solution with the Wittig reagent E. J. Corey et al, *JACS*, 91 5675 (1969) also Example 42 prepared from 13.3 g. (30 moles) of 4-carboxybutyltriphenylphosphonium bromide 2.52 g. (60 moles) of 57% sodium hydride dispersion, and 70 ml. of DMSO at $16°$ C. during 1 minute.

The solution is stirred at ambient temperature for 20 hours and poured into a stirred mixture of methylene chloride, ice, and hydrochloric acid. The organic phase is separated, and the aqueous phase is extracted with methylene chloride, saturated with sodium chloride, and extracted with ether. The combined organic extracts are partitioned with sodium bicarbonate. The aqueous basic extract is acidified with dilute HCl, saturated with sodium chloride, and extracted with ethyl acetate. The extract is washed with brine, dried over magnesium sulfate, and concentrated to give the crude title compound as an orange oil.

EXAMPLE 39

Preparation of all-cis-2-(6-carboxy-2-cis-hexenyl)-3,4-oxidocyclopentanone

To a stirred solution of ca. 1.6 moles of crude all-cis-2-(6-carboxy-2-cis-hexenyl)-3,4-oxidocyclopentanol (Example 38) in 1.6 ml. of ether is added 1.6 ml. of 4.0N chromic acid in 4N sulfuric acid at $0°$ C. during 9 minutes. After stirring for 5 minutes at $0°$ C. the solution is diluted with brine, ether, and ethyl acetate. The organic phase is treated with isopropanol, washed with brine and dried over magnesium sulfate. Evaporation of the solvent gives the subject compound as an oil.

EXAMPLE 40

Preparation of 2-(6-carboxy-2-cis-hexenyl)-4-hydroxycyclopent-2-en-1-one

A solution of 1.0 mmole of all-cis-2-(6-carboxy-2-cis-hexenyl)-3,4-oxidocyclopentanone (Example 39) and 3.0 mmoles of sodium carbonate in 15 ml. of water is allowed to stand at room temperature for 3 hours. The solution is acidified with HCl, saturated with sodium chloride, and extracted with ether. The extract is washed with brine, dried over magnesium sulfate, and concentrated to give a mixture of the title compound and the isomeric compound, 2-(6-carboxy-2-cis-hexenyl)-3-hydroxycyclopent-4-en-1-one. Further treatment of this mixture with N/10 sodium hydroxide at room temperature for 30 minutes causes the rearrangement of the latter isomer to the title compound, which is isolated from basic solution as above.

EXAMPLE 41

Preparation of
2-(6-carboxy-2-cis-hexenyl)-4-hydroxycyclopent-2-en-1-one

Treatment of cis-anti-cis-5-hydroxy-2,3-oxidocyclopentylacetaldehyde-γ-lactol (E. J. Corey and R. Noyori *Tetrahedron Letters,* 1070, 311) with 4-carboxybutyltriphenylphosphonium bromide as described in Example 38 is productive of 2β-(6-carboxy-2-cis-hexenyl)-3α,4α-oxidocyclopentan-1β-ol which on oxidation by the method of Example 39 provides 2β-(6-carboxy-2-cis-hexenyl)-3α,4α-oxidocyclopentanone, which in time on treatment with aqueous base by the procedure of Example 40 furnishes the subject compound.

EXAMPLE 42

Preparation of 4-carboxybutyltriphenylphosphonium bromide

A mixture of 103 g. of 5-bromovaleric acid and 152 g. of triphenylphosphine in 400 ml. of acetonitrile is refluxed for 48 hours, cooled, diluted with 100 ml. of benzene and allowed to crystallize. The crystals are filtered, washed with benzene and ether, to yield colorless material, m.p. 207°–209° C.

EXAMPLES 43–45

Treatment of the indicated ω-bromoalkanoic acids of Table 1 below with triphenylphosphine by the method described in Example 42 produces the phosphonium bromides of the table.

TABLE 1

| Example | Starting ω-bromo-alkanone acid | Product Phosphonium bromide |
|---|---|---|
| 43 | 4-bromo-n-butyric acid | 3-carboxypropyltriphenylphosphonium bromide |
| 44 | 6-bromo-n-hexanoic acid | 5-carboxypentyltriphenylphosphonium bromide |
| 45 | 7-bromo-n-heptanoic acid | 6-carboxyhexyltriphenylphosphonium bromide |

EXAMPLES 46–48

Treatment of all cis-5-hydroxy-2,3-oxidocyclopentylacetaldehyde-γ-lactol with the Wittig reagent prepared from the indicated phosphonium bromides of Table 2 below, all by the procedure of Example 38 is productive of the product compounds of the table.

TABLE 2

| Example | Reagent phosphonium bromide of Example | Product 3,4-oxidocyclopentanol |
|---|---|---|
| 46 | 43 | all cis-2-(5-carboxy-2-cis-pentenyl)-3,4-oxidocyclopentan-1-ol |
| 47 | 44 | all cis-2-(7-carboxy-2-cis-heptenyl)-3,4-oxidocyclopentan-1-ol |
| 48 | 45 | all cis-2-(8-carboxy-2-cis-octenyl)-3,4-oxidocyclopentan-1-ol |

EXAMPLES 49–51

Oxidation of the cyclopentanols indicated in Table 3 below by the method described in Example 39 furnishes the corresponding product 3,4-oxidocyclopentanones of the table.

TABLE 3

| Example | Starting cyclopentan-1-ol of Example | Product 3,4-oxidocyclopent-an-1-one |
|---|---|---|
| 49 | 46 | all-cis-2-(5-carboxy-2-cis-pentenyl)-3,4-oxidocyclopentan-1-one |
| 50 | 47 | all cis-2-(7-carboxy-2-cis-heptenyl)-3,4-oxidocyclopentan-1-one |
| 51 | 48 | all cis-2-(8-carboxy-2-cis-octenyl)-3,4-oxidocyclopentan-1-one |

EXAMPLES 52–54

Alkaline treatment of the 3,4-oxidocyclopentanones of Table 4 below by the process described in Example 40 is productive of the 4-hydroxycyclopentenones of the table.

TABLE 4

| Example | Starting 3,4-oxidocyclopentanone of Example | Product 4-hydroxycyclopent-2-en-1-one |
|---|---|---|
| 52 | 49 | 2-(5-carboxy-2-cis-pentenyl)-4-hydroxycyclopent-2-en-1-one |
| 53 | 50 | 2-(7-carboxy-2-cis-heptenyl)-4-hydroxycyclopent-2-en-1-one |
| 54 | 51 | 2-(8-carboxy-2-cis-octenyl)-4-hydroxycyclopent-2-en-1-one |

EXAMPLES 55–58

Treatment of the 4-hydroxycyclopent-2-en-1-ones listed in Table 5 below with dihydropyran (in the manner of Example 3) is productive of the corresponding bis-tetrahydropyranyl ether-esters of the table.

TABLE 5

| Example | Starting 4-hydroxycyclopent-2-en-1-one of Example | Product bis-tetrahydropyranyl ether-ester |
|---|---|---|
| 55 | 40 | 4-tetrahydropyranyloxy-2-(6-carbotetrahydropyranyloxy-2-cis-hexenyl)cyclopent-2-en-1-one |
| 56 | 52 | 4-tetrahydropyranyloxy-2-(5-carbotetrahydropyranyloxy-2-cis-pentenyl)cyclopent-2-en-1-one |
| 57 | 53 | 4-tetrahydropyranyloxy-2-(7-carbotetrahydropyranyloxy-2-cis-heptenyl)-cyclopent-2-en-1-one |
| 58 | 54 | 4-tetrahydropyranyloxy-2-(8-carbotetrahydropyranyloxy-2-cis-octenyl)-cyclopent-2-en-1-one |

EXAMPLES 59–63

Treatment of the 4-hydroxycyclopent-2-en-1-ones listed in Table 6 below with the indicated trialkylsilyl chloride by the method described in Example 32 is productive of the bis-trialkylsilyl ether-esters of the table.

TABLE 6

| Example | Starting 4-hydroxy-cyclopentenone of Example | Trialkylsilyl-chloride | Product bis-trialkylsilyl ether-ester |
|---|---|---|---|
| 59 | 40 | $(CH_3)_3SiCl$ | 4-trimethylsiloxy-2-(6-carbotrimethyl-siloxy-2-cis-hexenyl)cyclopent-2-en-1-one |
| 60 | 52 | $(CH_3)_3SiCl$ | 4-trimethylsiloxy-2-(5-carbotrimethyl-siloxy-2-cis-pentenyl)cyclopent-2-en-1-one |
| 61 | 53 | $(CH_3)_3SiCl$ | 4-trimethylsiloxy-2-(7-carbotrimethyl-siloxy-2-cis-heptenyl)cyclopent-2-en-1-one |
| 62 | 54 | $(CH_3)_3SiCl$ | 4-trimethylsiloxy-2-(8-carbotrimethyl-siloxy-2-cis-octenyl)cyclopent-2-en-1-one |
| 63 | 40 | dimethyliso-propyl silyl chloride | 4-dimethylisopropylsiloxy-2-(6-carbodi-methylisopropylsiloxy-2-cis-hexenyl)cyclo-pent-2-en-1-one |

EXAMPLES 64–72

Treatment of the ether-ester blocked 4-oxycyclopent-2-en-1-ones listed in Table 7 below with lithium trimethyl[3-(p-anisyldiphenylmethoxy)-trans-1-octenyl] according to the procedure described in Example 35 is productive of the 9-oxo-11α,15-dihydroxy-5-cis,13-trans-prostadienoic acids of the table as well as the corresponding 15-epi derivatives, separable from the listed 15-normal derivatives by chromatography.

TABLE 7

| Example | Starting blocked 4-oxycyclopent-2-en-1-one of Example | 9-oxo-11α, 15-dihydroxy-5-cis, 13-trans-prostadienoic acids |
|---|---|---|
| 64 | 55 | 9-oxo-11α, 15-dihydroxy-5-cis, 13-trans-prosta-dienoic acid (prostaglandin $E_2$) |
| 65 | 59 | 9-oxo-11α, 15-dihydroxy-5-cis, 13-trans-prosta-dienoic acid (prostaglandin $E_2$) |
| 66 | 63 | 9-oxo-11α, 15-dihydroxy-5-cis, 13-trans-prosta-dienoic acid (prostaglandin $E_2$) |
| 67 | 56 | 9-oxo-11α, 15-dihydroxy-4-nor-5-cis, 13-trans-prostadienoic acid |
| 68 | 60 | 9-oxo-11α, 15-dihydroxy-4-nor-5-cis, 13-trans-prostadienoic acid |
| 69 | 57 | 9-oxo-11α, 15-dihydroxy-4a-homo-5-cis, 13-trans-prostadienoic acid |
| 70 | 61 | 9-oxo-11α, 15-dihydroxy-4a-homo-5-cis, 13-trans-prostadienoic acid |
| 71 | 58 | 9-oxo-11α, 15-dihydroxy-4a, 4b-homo-5-cis, 13-trans-prostadienoic acid |
| 72 | 62 | 9-oxo-11α, 15-dihydroxy-4a, 4b-homo-5-cis, 13-trans-prostadienoic acid |

EXAMPLE 73

Preparation of 9-oxo-11α,15-dihydroxy-5-cis,13-cis-prostadienoic acid

Treatment in the manner described in Example 26 of 4-tetrahydropyranyloxy-2-(6-carbotetrahy-dropyranyloxy-2-cis-hexenyl)cyclopent-2-en-1-one (Example 55) with the Grignard reagent prepared from magnesium and 1-bromo-3-triphenylmethoxy-trans-1-octene (Example 22) also as described in Example 26 in the presence of cuprous iodide tri-n-butylphosphine complex is productive, after chromatography, of prostaglandin $E_2$ and 9-oxo-11α,15-dihydroxy-5-cis,13-cis-prostadienoic acid.

EXAMPLE 74

Preparation of 1-iodo-trans-1-octen-3-ol

A solution of 78.2 g. (0.310 moles) of 1-iodo-trans-1-octen-3-one (Example 19) in 150 ml. of absolute ethanol is added dropwise over 2 hours to a slurry of 6.49 g. (0.172 moles) of sodium borohydride in 50 ml. of absolute ethanol cooled in an ice bath. After the addition is complete, the mixture is stirred for 2 hours with ice cooling and is then poured into 1 l of water. The mixture is extracted into benzene and the organic phase is washed with saturated brine, dried ($Na_2SO_4$) and evaporated. The resulting oil is dissolved into 400 ml. of absolute ethanol and treated with 5 mole percent of p-carboxyphenylhydrazine at 70° C. for 1.5 hours to remove residual ketone. The mixture is cooled and evaporated and the residue is dissolved into 400 ml. of ether and is filtered. The filtrate is washed with dilute sodium bicarbonate solution and saturated brine, dried ($Na_2SO_4$), and evaporated to an oil. This oil is chromatographed upon 2 kg. of Florisil ® packed in hexane and the product is obtained upon elution with benzene. Distillation of the product yields a colorless oil, b.p. 74°–76° C. (0.005 tor.).

What is claimed is:

1. A compound of the formula $$\text{[structure: cyclopentenone with } CH_2-CH=CH-(CH_2)_p-COR_1 \text{ (cis) substituent and R group]}$$

wherein $R_1$ is $C_1$–$C_4$ alkyl R is selected from the group consisting of

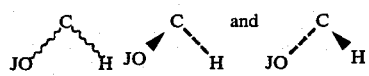

wherein J is tri-$C_1$–$C_4$-lower alkyl silyl, and p is 2–4.

2. The compound of claim 1 wherein $R_1$ is methyl.

3. The compound of claim 1 wherein J is trimethylsilyl.

4. The compound of claim 1, 2 or 3 wherein p is 3.

5. The compound of claim 1 which is 2-(7-carbomethoxyhex-2-cis-en-1-yl)-4RS-trimethylsiloxy-2-cyclopenten-1-one.

6. The compound of claim 1 which is 2-(7-carbomethoxyhex-2-cis-en-1-yl)-4R-trimethylsiloxy-2-cyclopenten-1-one.

* * * * *